United States Patent [19]

Whitten et al.

[11] Patent Number: 5,554,773
[45] Date of Patent: Sep. 10, 1996

[54] N-TRITYL PROTECTED ASPARTIC ACID DERIVATIVES FOR THE PREPARATION OF PHOSPHONATE NMDA ANTAGONISTS

[75] Inventors: Jeffrey P. Whitten, Cincinnati; Duane E. Rudisill, West Chester, both of Ohio

[73] Assignee: Merrell Pharmaceuticals Inc., Cincinnati, Ohio

[21] Appl. No.: 439,672

[22] Filed: May 12, 1995

Related U.S. Application Data

[62] Division of Ser. No. 341,325, Nov. 16, 1994, abandoned, which is a continuation of Ser. No. 45,832, Apr. 9, 1993, abandoned, which is a continuation-in-part of Ser. No. 792,834, Nov. 15, 1991, abandoned.

[51] Int. Cl.$^6$ .................................................. C07F 9/40
[52] U.S. Cl. ................................. 552/104; 558/169
[58] Field of Search ........................... 558/169; 552/104

[56] References Cited

U.S. PATENT DOCUMENTS 5,095,009  3/1992  Whitten et al. ................ 514/85
5,179,085  1/1993  Bigge et al. .................... 514/114

FOREIGN PATENT DOCUMENTS 0418863  3/1991  European Pat. Off. .

OTHER PUBLICATIONS

Tetrahedron Letter, vol. 28, No. 6, pp. 611–612, 1987, P. K. Chakravarty, et al.
J. Org. Chem. 1986, 51, 3882–3890; Paul L. Feldman, et al.
J. Org. Chem., 1990, 55, 3068–3074, Peter Gmeiner, et al.
Baldwin et al., Tetrahedron, 44 (2), pp. 637–642 (1988).
Webb et al., J. Org. Chem, 34 (3), pp. 576–580 (1969).

*Primary Examiner*—Gary Geist
*Assistant Examiner*—Barbara S. Frazier
*Attorney, Agent, or Firm*—J. Michael Dixon

[57] ABSTRACT

The present invention related to novel (R)-dimethyl N-tritylaspartate and novel (R)-alkyl N-trityl-4-oxo-5-phosphononorvalinate derivatives which are useful in the preparation of the class of beta-ketophosphonate NMDA antagonists.

7 Claims, No Drawings

N-TRITYL PROTECTED ASPARTIC ACID DERIVATIVES FOR THE PREPARATION OF PHOSPHONATE NMDA ANTAGONISTS

This is a division, of application Ser. No. 08/341,325, filed Nov. 16, 1996, now abandoned, which is a continuation of application Ser. No. 08/045,832 filed Apr. 9, 1993, now abandoned which is a continuation in part of application Ser. No. 07/792,834, filed Nov. 15, 1991, now abandoned, herein incorporated by reference.

The present invention is related to novel (R)-dimethyl N-tritylaspartate and novel (R)-alkyl N-trityl-4-oxo-5-phosphononorvalinate derivatives which are useful in the preparation of a class of beta-ketophosphonate NMDA antagonists.

The class of beta-ketophosphonate NMDA antagonists are important in the treatment of epilepsy, nerve trauma such as that caused by stroke, cardiac arrest, hypoglycemia, and physical damage to either the brain or spinal cord, neurogenerative diseases, anxiety and for the relief of pain [European Application No. 91107955.6 of Jeffrey P. Whitten entitled Heterocyclic-NMDA Antagonists, filed May 16, 1991]. This class of excitatory amino acid antagonists which act at the NMDA receptor complex can be described by formula I wherein R is hydrogen, methyl or ethyl:

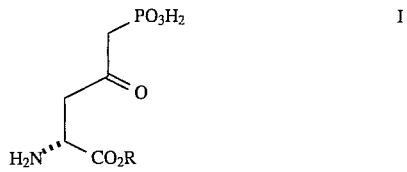

(R)-4-Oxo-5-phosphononorvaline derivatives of formula I have been synthesized by protecting (R)-aspartic acid as the CBZ oxazolone, converting the resulting acid to an acid chloride and then coupling with a cuprate to form the betaketophosponate. A two step deprotection yielded the desired (R)-4-oxo-5-phosphononorvaline derivative of formula I after chromatography.

The novel (R)-dialkyl N-tritylaspartate and novel (R)alkyl N-trityl-4-oxo-5-phosphononorvalinate derivatives of the present invention are useful in the preparation of the class of beta-ketophosphonate NMDA antagonists. These compounds afford the (R)-4-oxo-5-phosphononorvaline derivatives of formula I with a high retention of chirality from readily available (R)-aspartic acid. In addition, the use of the novel (R)-dialkyl N-tritylaspartate and novel (R)-alkyl N-trityl-4-oxo-5-phosphononorvalinate derivatives of the present invention allows for a shorter synthesis with higher yields and avoids the use of copper. Further, the use of (R)-dimethyl N-tritylaspartate and (R)-methyl N-trityl-4-oxo-5-phosphononorvalinate derivatives of the present invention provides stable crystalline materials at every step thereby avoiding the necessity of chromatography.

SUMMARY OF THE INVENTION

The present invention provides novel (R)-dialkyl N-tritylaspartate of formula II and novel (R)-alkyl N-trityl-4-oxo-5-phosphonovalinate derivatives of formula III.

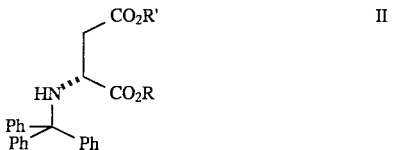

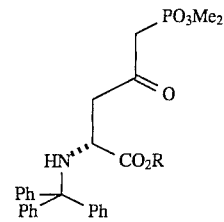

wherein R and R' are simultaneously methyl or ethyl.

The present invention further provides a method of using (R)-dialkyl N-tritylaspartate of formula II comprising the steps of (a) reacting (R)-dialkyl N-tritylaspartate of formula II with an appropriate metallo dimethyl methylphosphonate to give a (R)-alkyl N-trityl-4- oxo-5-phosphononorvalinate derivative of formula III and (b) reacting said (R)-alkyl N-trityl-4-oxo-5phosphononorvalinate derivative of formula III with a suitable aqueous acid or trimethylsilyl iodide. It is preferred that R and R' are simultaneously methyl. As used herein, Ph represents an unsubstituted phenyl ring.

The present invention further provides a process for preparing the (R)-4-oxo-5-phosphononorvaline derivatives of formula I comprising the steps of (a) reacting (R)-dialkyl N-tritylaspartate of formula II with an appropriate metallo dimethyl methylphosphonate to give a (R)-alkyl N-trityl-4-oxy-5-phosphononorvalinate derivative of formula III and (b) reacting said (R)-alkyl N-trityl-4-oxo-5phosphononorvalinate derivative of formula III with a suitable acid or a suitable trimethylsilyl halide. It is preferred that R and R' are simultaneously methyl.

DETAILED DESCRIPTION OF THE INVENTION

The novel (R)-dialkyl N-tritylaspartate of formula II and novel (R)-alkyl N-trityl-4-oxo-5-phosphononorvalinate derivatives of formula III can be prepared by utilizing procedures and techniques well known and appreciated by one of ordinary skill in the art. A general synthetic procedure for preparing these compounds is set forth in Scheme A.

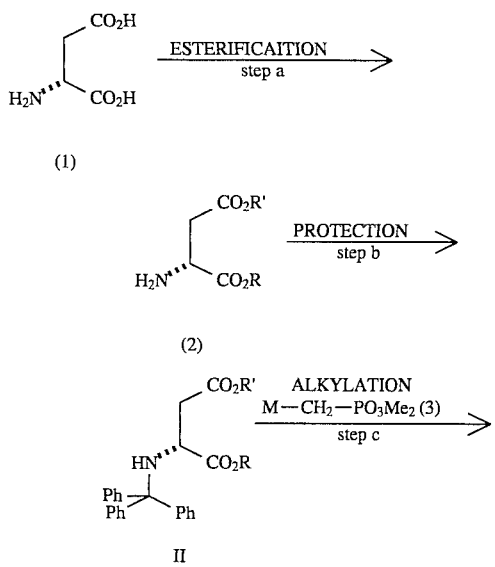

-continued
Scheme A

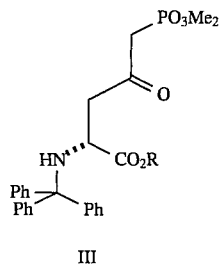

III

Scheme A provides a synthetic procedure for preparing (R)-dialkyl N-tritylaspartate of formula II and novel (R)-alkyl N-trityl-4-oxo-5-phosphononorvalinate derivatives of formula III.

In step a, (R)-aspartic acid (1) is esterified to give (R)-dialkylaspartate (2) by techniques and procedures well known and appreciated by one of ordinary skill in the art. For example, (R)-aspartic acid (1) is converted to (R)-dialkylaspartate (2) by adding a suitable activating agent, such as thionyl chloride, to a suspension of the (R)-aspartic acid (1) in a suitable alcohol such as methanol or ethanol. The reactants are typically stirred together for a period of time ranging from 10 hours to 3 days and at a temperature range of from 0° C to room temperature. The resulting (R)-dialkylaspartate (2) is recovered from the reaction zone by evaporation of the solvent.

In step b, (R)-dialkyaspartate hydrochloride (2) is converted to the (R)-dialkyl N-tritylaspartate of formula II by treating (R)-dialkylaspartate hydrochloride (2) with triphenylmethyl chloride and a suitable base, such as triethylamine. The reactants are typically contacted in a suitable organic solvent such as acetonitrile. The reactants are typically stirred together at room temperature for a period of time ranging from 2–24 hours. The resulting (R)-dialkyl N-tritylaspartate of formula II is recovered from the reaction zone by extractive methods as is known in the art.

In step c, the (R)-dialkyl N-tritylaspartate of formula II is converted to the (R)-alkyl N-trityl-4-oxo-5phosphononorvalinate derivatives of formula III by treating the (R)-dialkyl N-tritylaspartate of formula II with a suitable metallo methyl dimethylphosphonate of structure (3). Suitable metallo compounds of structure (3) include lithium methyl dimethylphosphonate, potassium methyl dimethylphosphonate, sodium methyl dimethylphosphonate, magnesium methyl dimethylphosphonate and the like. The reactants are typically contacted in a suitable anhydrous organic solvent such as tetrahydrofuran. The reactants are typically stirred together for a period of time ranging from 15 minutes to 5 hours and at a temperature range of from –78° C. to –40° C. The (R)-alkyl N-trityl-4-oxo-5phosphononorvalinate derivatives of formula III is recovered from the reaction zone by acid neutralization followed by extractive methods as is known in the art. It may be purified by recrystallization.

Starting materials for use in Scheme A are readily available to one of ordinary skill in the art. The synthesis outlined above in Reaction Scheme A produces compounds II and III as the essentially pure R-enantiomers. As used in this application the phrase essentially pure means that the L-enantiomer is not present at a concentration greater than 3% w/w. More preferably it is not present at a concentration greater than 2% w/w.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "µL" refers to microliters; "µg" refers to micrograms; and "µM" refers to micromolar.

EXAMPLE 1

(R)-Dimethyl N-tritylaspartate

Step a: (R)-Dimethylaspartate hydrochloride

Suspend (R)-aspartic acid (39.9g, 0.30mol) in methanol (250mL), cool to 0° C. and place under a nitrogen atmosphere. Add, by dropwise addition over 0.5 hours, thionyl chloride (50.1g, 0.42mol). Allow to warm to room temperature and stir for 48 hours. Evaporate the solvent, triturate the residue with ether and collect by filtration to give the title compound as a white solid (60.1g, 100%). $^1$H NMR (DMSO-$d_6$) δ4.3 (t, 1H), 3.75 (s, 3H), 3.67 (m, 2H).

Step b: (R)-Dimethyl N-tritylaspartate Mix (R)-dimethyl aspartate hydrochloride (57g, 0.288mol), triphenylmethylchloride (75.0g, 0.27mol) and acetonitrile. Stir well and add, by dropwise addition over 2 hours, triethylamine (85mL, 0.27mol). Stir the resulting mixture for a further 4 hours then add ethyl acetate (500mL). Wash with saturated sodium chloride (500mL) and add chloroform (100mL). Separate the organic phase, dry (Na2SO4) and evaporate to a residue. Add methanol (250mL) and stir to effect crystallization. Filter to give the title compound as a white solid (83g, 74%). $^1$H NMR (CDCl$_3$) δ7.5–7.25 (m, 15H), 4.78 (m, 1H), 4.72 (s, 3H), 3.3 (s, 3H), 2.95 (bs, 1H), 2.62 (m, 2H).

EXAMPLE 2

(R)-Methyl N-trityl-4-oxo-5-(dimethylphosphono)norvalinate

Dissolve dimethyl methylphosphonate (83mL, 0.766 mol) in anhydrous tetrahydrofuran (800 mL), cool to –78° C. and place under an inert atmosphere. Add, by dropwise addition over 15 minutes, n-butyllithium (306 mL of a 2.5M solution, 0,766 mol). Stir the resulting clear solution for a further 0.5 hour. While maintaining the solution at –78° C, add by dropwise addition over 15 minutes, to another solution of (R)-dimethyl N-tritylaspartate (71 g, 0.182 mol) in anhydrous tetrahydrofuran (200 mL) also at –78° C. Stir for a further 0.5 hours, quench with acetic acid (45 mL) and warm to room temperature. Add ethyl acetate (500 mL) and saturated sodium bicarbonate (250 mL). Separate the organic phase, filter through silica gel and evaporate the solvent to give a solid residue. Crystallize (t-butylmethyl ether/hexane) to give the title compound as a white solid (61.0 g, 69%). $^1$H NMR (CDCl$_3$) δ7.5–7.25 (m, 15 H), 3.82 (s, 3H), 3.79 (s, 3H), 3.75 (t, 3H), 3.08 (d, 2H), 2.88 (m, 2H), 1.65 (bs, 1H).

The (R)-4-oxo-5-phosphononorvaline derivatives of formula I can be prepared from the (R)-alkyl N-trityl-4-oxo-5-phosphononorvalinate derivative of formula III as set forth in Scheme B.

Scheme B

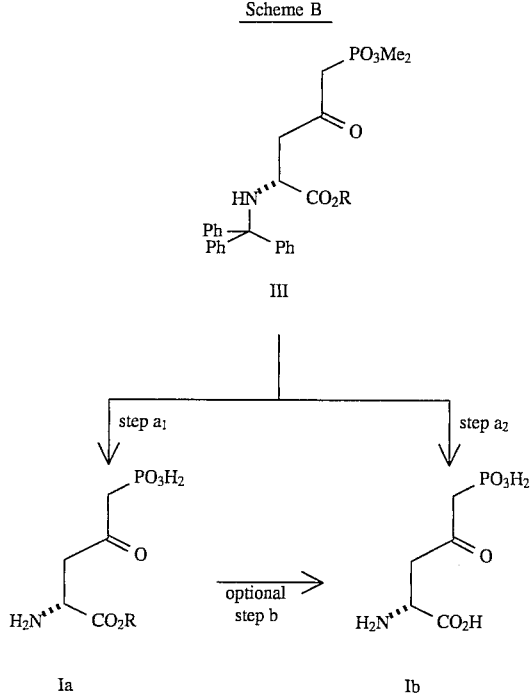

Scheme B provides a general method for using the (R)alkyl N-trityl-4-oxo-5-phosphononorvalinate derivatives of formula III in order to form the (R)-4-oxo-5phosphononorvaline derivatives of formula I.

In step $a_1$, the phosphonate methyl ester functionalities of the appropriate (R)-alkyl N-trityl-4-oxo-5-phosphononorvalinate derivatives of formula III are cleaved to give the corresponding (R)-4-oxo-5phosphononorvaline derivative of formula Ia.

For example, the appropriate (R)-alkyl N-trityl-4-oxo-5-phosphononorvalinate derivative of formula III is treated with two molar equivalents of a suitable trimethylsilyl halide such as trimethylsilyl iodide or trimethylsilyl bromide. The reactants are typically contacted in a suitable organic solvent such as acetonitrile or methylene chloride. The reactants are typically stirred together at room temperature for a period of time ranging from 2–10 hours. The resulting (R)-4-oxo-5-phosphononorvaline derivative of formula Ia is recovered from the reaction zone by extractive methods as is known in the art. It may be purified by chromatography.

In step $a_2$, the phosphonate methyl ester and carboxylate functionalities of the appropriate (R)-alkyl N-trityl- 4-oxo-5-phosphononorvalinate derivatives of formula III are cleaved to give the corresponding (R)-4-oxo-5-phosphononorvaline derivative of formula Ib.

For example, the appropriate (R)-alkyl N-trityl-4-oxo-5-phosphononorvalinate derivative of formula III is treated with a suitable strong aqueous mineral acid, such as hydrochloric acid, hydrobromic acid, sulfuric acid and the like. The reactants are typically stirred together for a period of time ranging from 5 minutes to 2 hours and at a temperature range of from room temperature to reflux. The resulting (R)-4-oxo-5-phosphononorvaline derivative of formula Ib is recovered from the reaction zone as its hydrochloride salt by evaporation of the solvent. It may be converted to its free base by treatment with propylene oxide as is known in the art.

In optional step b, the carboxylate functionality of the appropriate (R)-4-oxo-5-phosphononorvaline derivative of formula Ia is cleaved to give the (R)-4-oxo-5-phosphononorvaline derivative of formula Ib as described previously in step $a_2$.

The following example presents a typical method of using the (R)-alkyl N-trityl-4-oxo-5-phosphononorvalinate derivatives of formula III in order to form the (R)-4-oxo-5-phosphononorvaline derivatives of formula I. This example is understood to be illustrative only and is not intended to limit the scope of the present invention in any way.

EXAMPLE 3

(R)-4-Oxo-5-phosphononorvaline Add (R)-methyl N-trityl-4-oxo-5(dimethylphophono)-norvalinate (1.0 g, 2.02 mmol) to aqueous 5M hydrochloric acid (10 mL) and reflux for 15 hours. Evaporate the resulting solution to give a residue and take the residue up in methanol (8 mL). Add propylene oxide (0.5 mL) and stir for 0.5 hours. Filter the resulting solid and wash with methanol (5 mL). Take the resulting solid up in water (30 mL) and freeze dry to give the title compound as a white solid.

$^1$H NMR ($D_2O$, 300 MHz) 4.3 (m, 1H), 3.48 (m, 2H), 3.12 (m, 2H);

$^{13}$C NMR ($D_2O$, 300 MGz) 208.283, 175,121, 52.161, 52.110, 46,106;

$^{31}$P NMR ($D_2O$, 121 MHz) 12.4;

MS (FAB) m/e 212 (M+H+), 167 (M+H$^+$–HCO$_2$H), 139 (+H$_3$PO$_3$CH$_2$COCH$_3$), 132 (+CH$_3$COCH$_2$CH(NH$_3$+)CO$_2$H).

Anal. Calcd for $C_5H_{10}NO_6 \cdot 0.5H_2O$: C, 27.28; H, 5.04; N, 6.45;

Found: C, 27.38; H, 4.77; N, 645 (Tg% loss=4.4).

What is claimed is:

1. R-enantiomers of the formula:

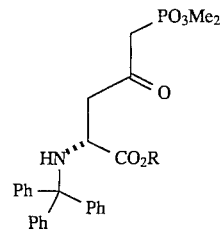

wherein R is methyl or ethyl.

2. A compound according to claim 1 present as an essentially pure R-enantiomer.

3. The compound; (R)-Methyl N-trityl-4-oxo-5(dimethylphosphono)norvalinate.

4. A compound according to claim 1 in which R is methyl.

5. A compound according to claim 2 in which R is methyl.

6. A compound according to claim 1 in which R is ethyl.

7. A compound according to claim 2 in which R is ethyl.

* * * * *

UNITED STATES PATENT AND TRADEMARK OFFICE
CERTIFICATE OF CORRECTION

PATENT NO. : 5,554,773

DATED : Sep. 10, 1996

INVENTOR(s) : Whitten et al.

It is certified that error appears in the above-identified patent and that said Letters Patent is hereby corrected as shown below:

Column 1, line 6 of patent reads "Nov. 16, 1996" and should read -- Nov. 16, 1994 -- ..

Column 4, line 33 of patent reads "(Na2SO4)" and should read -- $(Na_2SO_4)$ --.

Signed and Sealed this

Twenty-first Day of July, 1998

Attest:

BRUCE LEHMAN

*Attesting Officer*

*Commissioner of Patents and Trademarks*